United States Patent [19]
Tascon et al.

[11] Patent Number: 5,080,669
[45] Date of Patent: Jan. 14, 1992

[54] PROSTHETIC HEART VALVE

[75] Inventors: Manuel Tascon, 38 Royal St. George Rd., Newport Beach, Calif. 92660; Jack C. Bokros, Austin, Tex.

[73] Assignees: Manuel Tascon, Newport Beach, Calif.; Carbon Implants, Inc., Austin, Tex.

[21] Appl. No.: 478,417

[22] Filed: Feb. 12, 1990

[51] Int. Cl.$^5$ ............................................. A61F 2/24
[52] U.S. Cl. ..................................... 623/2; 137/512.1; 137/527
[58] Field of Search .............. 623/2; 137/512.1, 527.8, 137/527

[56] References Cited

U.S. PATENT DOCUMENTS

| | | | |
|---|---|---|---|
| 3,859,668 | 1/1975 | Anderson | 3/1 |
| 4,078,268 | 3/1978 | Possis | 3/1.5 |
| 4,159,543 | 7/1979 | Carpentier | 3/1.5 |
| 4,178,639 | 12/1979 | Bokros | 3/1.5 |
| 4,306,319 | 12/1981 | Kaster | 3/1.5 |
| 4,328,592 | 5/1982 | Klawitter | 3/1.5 |
| 4,357,715 | 11/1982 | Klawitter | 3/1.5 |
| 4,846,830 | 7/1989 | Knoch et al. | 623/2 |
| 4,863,467 | 9/1989 | Bokros | 623/2 |
| 4,880,010 | 12/1989 | Bokros | 623/2 |

Primary Examiner—David J. Isabella
Assistant Examiner—Stephanie L. Iantorno
Attorney, Agent, or Firm—Fitch, Even, Tabin & Flannery

[57] ABSTRACT

Disclosed is a heart valve of the pivotal bi-leaflet or single occluder type having improved washing characteristics in the region of the support arrangement. The leaflets include cylindrical, or other circular cross-sectional, pivot enlargements at opposite sides of the leaflets, and the valve body includes a number of projections extending inward from its sidewall. The leaflets are mounted in the valve body such that the projections encircle the pivot enlargements at the opposing ends of the leaflets, thereby confining their movement to substantially pivotal rotation between open and closed positions. The projections are spaced from one another, with the region between adjacent projections defining channels through which blood can flow. Some blood flows through these channels both when the valve is in its open position and its closed position, thereby providing blood flow across the pivot enlargements and projections and, thus, minimizing stagnation in the region of the support arrangement.

19 Claims, 2 Drawing Sheets

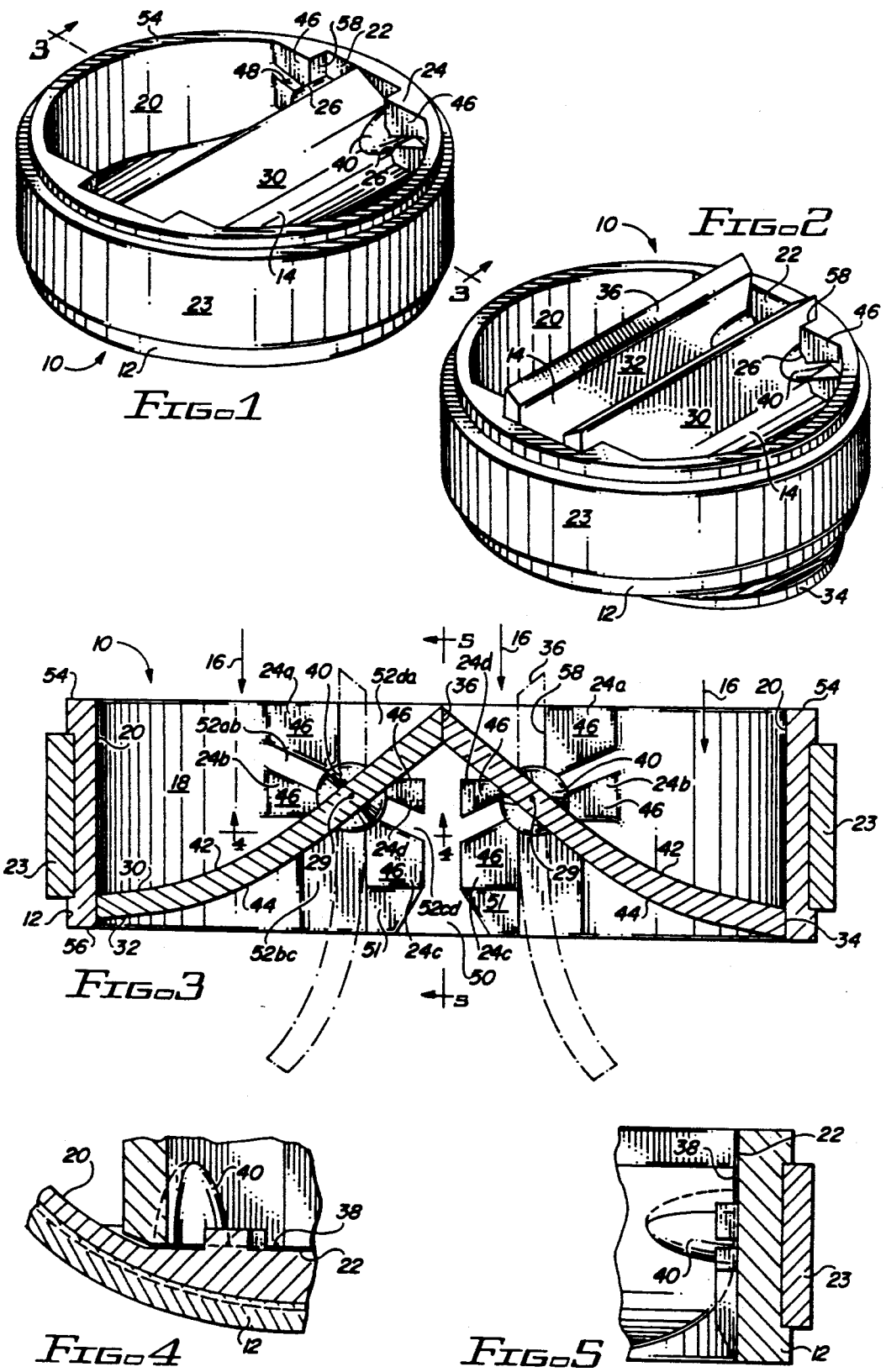

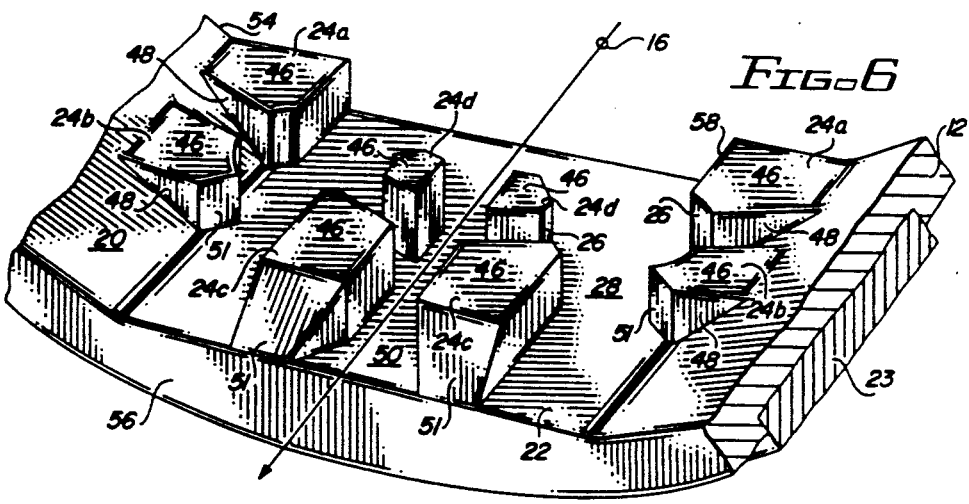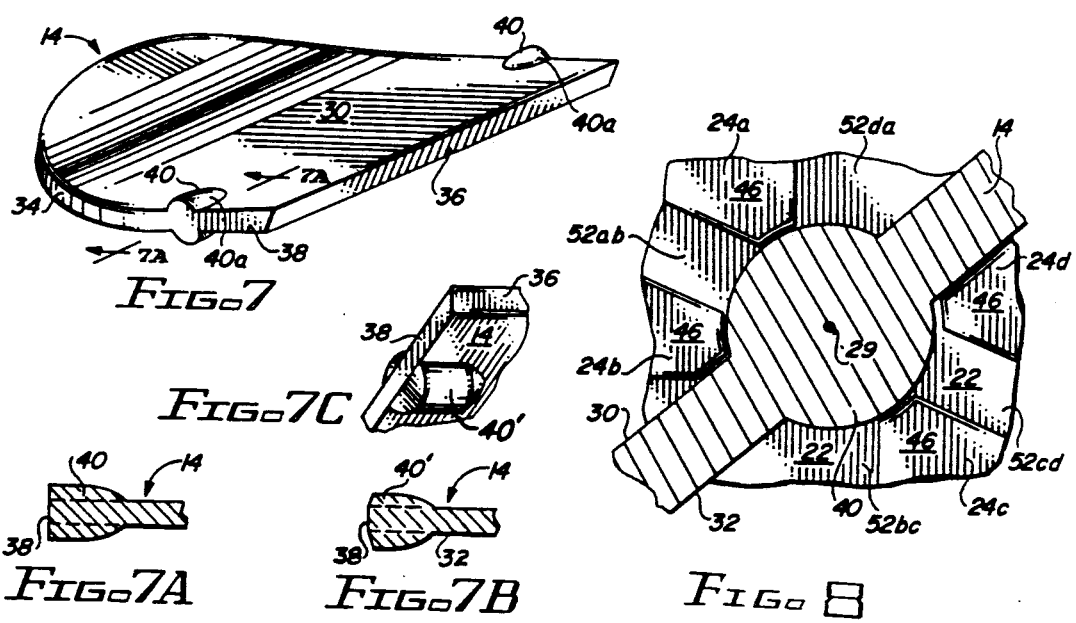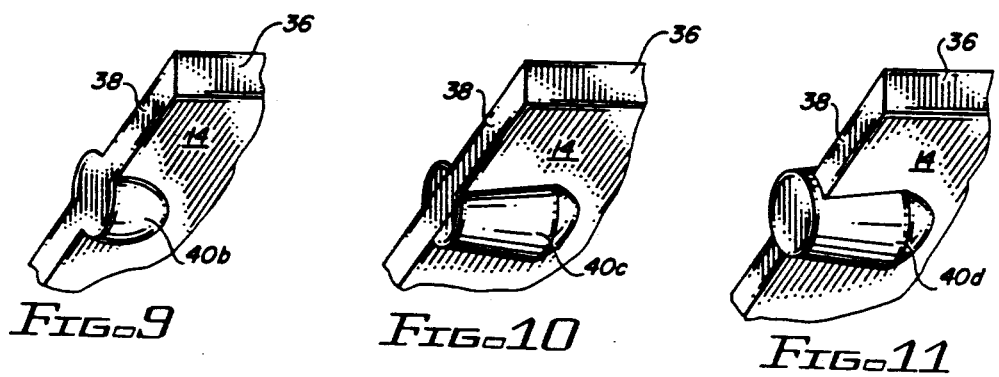

PROSTHETIC HEART VALVE

BACKGROUND OF THE INVENTION

The present invention pertains to heart valve prostheses and in particular, to "mechanical" prosthetic heart valves that may use pivoting bi-leaflet valve members.

DESCRIPTION OF THE PRIOR ART

Various types of heart valve prostheses have been developed which operate hemodynamically as a result of the pumping action of the heart. Among the types of heart valves which have been developed are valves utilizing various support arrangements for connecting pivoting valve members or leaflets to a valve body. A particular problem associated with all types of heart valve prostheses is stagnation within the valve in the region of the support arrangement, which eventually leads to clotting. This is a particular problem for pivoting valve members in the region where the pivot posts extend into corresponding recesses. Valves employing a spherical socket in the valve body and a spherical pivot surface in a bi-leaflet valve are shown in U.S. Pat. Nos. 4,178,639 and 4,328,592. These arrangements were also found to have some susceptibility to stagnation in the spherical socket of the valve body that could result in clotting in this region after prolonged usage.

To achieve greater washing of the valve in the region of the support arrangement, valves employing protrusions extending inward from the sidewall of an annular valve body to control the movement of leaflets by cooperating with enlargements on the lateral edges of the leaflets were designed. Such arrangements are shown in connection with single occluder valves in U.S. Pat. No. 3,859,668 and bi-leaflet valves in U.S. Pat. Nos. 4,078,268 and 4,159,543. However, these designs were still susceptible to blood coagulation in the region of the support arrangements because of inadequate washing, and the need continues for improved prosthetic heart valves for permanent implantation into the human heart.

In addition to preventing coagulation in the region of the support arrangement, a prosthetic heart valve should be rapidly responsive to blood flow to quickly open during the pumping stroke of the heart and to close quickly when the heart relaxes to prevent substantial regurgitation of the blood. In its open position, the heart valve should provide a passageway which is large and which has good flow characteristics so that blood flows freely therethrough without adverse boundary layer separation and with a minimum of drag. Additionally, the heart valve must, of course, be biocompatible and thrombo-resistant throughout, and in this regard, it is important that all surfaces be well washed to prevent stagnation which might lead to eventual clotting.

SUMMARY OF THE INVENTION

The present invention provides heart valves having the aforementioned desirable characteristics wherein the valve leaflets, or occluders, and the valve body are designed to eliminate stagnation in the region of the support arrangement connecting the leaflets and valve body.

These and other objects of the present invention, which will become apparent from studying the appended description and accompanying drawings, are provided in a prosthetic heart valve for allowing blood flow therethrough in a downstream direction. In accordance with the present invention there is provided a bi-leaflet, prosthetic heart valve which has improved washing characteristics in the region of the support arrangement. It will be readily apparent to those skilled in the art that the design can be employed with single occluder valves as well. The leaflets include cylindrical, or other circular cross-sectional, pivot enlargements at opposite sides of each leaflet, and the valve body includes a number of projections extending inward from its sidewall. The leaflets are mounted in the valve body such that the projections encircle the pivot enlargements at the ends of the leaflets, thereby confining their movement to substantially pivotal rotation between open and closed positions. The projections define channels in the regions between adjacent, inwardly extending projections from the valve body. These channels provide pathways through which blood can flow. Blood flow through such channels results in blood flow across the pivot enlargements at opposite sides of each leaflet and the valve body projections including the regions between these two, thus minimizing stagnation in the region of the support arrangement.

BRIEF DESCRIPTION OF THE DRAWINGS

In the drawings, wherein like elements referenced alike,

FIG. 1 is a perspective view of a bi-leaflet heart valve embodying various features of the present invention, shown in its closed position;

FIG. 2 is a perspective view of the valve of FIG. 1, shown in its open position;

FIG. 3 is an enlarged cross-sectional view of the heart valve taken along the line 3—3 of FIG. 1, showing the valve in its closed position;

FIG. 4 is a fragmentary, enlarged cross-sectional view of the valve taken along the line 4—4 of FIG. 3, particularly showing the support arrangement at the sidewall;

FIG. 5 is a fragmentary, enlarged cross-sectional view of the valve taken along the line 5—5 of FIG. 3, particularly showing the support arrangement at the sidewall;

FIG. 6 is a perspective fragmentary view of the valve of FIG. 1, particularly illustrating the projections extending inwardly from the flat wall sections of the valve body;

FIG. 7 is a perspective view of one leaflet from the valve of FIG. 1, having cylindrical pivot enlargements on opposite sides of the leaflet, the pivot enlargements being coterminous with the lateral sides of the leaflet;

FIG. 7A is a cross-sectional, fragmentary view of one embodiment of a pivot enlargement, the enlargement being coterminous with the leaflet lateral side;

FIG. 7B is a cross-sectional, fragmentary view similar to FIG. 7A of an alternative embodiment of a pivot enlargement at the lateral side of a leaflet, the enlargement being relayed along the leaflet lateral side;

FIG. 7C is a fragmentary perspective view of the leaflet shown in FIG. 7B illustrating the relief sections removed from the radially outer ends of the enlargements;

FIG. 8 is a cross-sectional, fragmentary view of a leaflet and the associated projections extending from the valve body showing the arrangement of the leaflet and projections with the valve in its closed position;

FIG. 9 is a perspective, fragmentary view of an alternative embodiment of a leaflet having spherical pivot enlargements on opposing lateral sides of the leaflet, the pivot enlargements being coterminous with the lateral sides of the leaflet;

FIG. 10 is a perspective, fragmentary view of another alternative embodiment of a leaflet, having conical pivot enlargements on opposing lateral sides of the leaflet, the pivot enlargements being coterminous with the lateral sides of the leaflet; and FIG. 11 is a perspective, fragmentary view of still another alternative embodiment of a leaflet, having conical pivot enlargements on opposing lateral sides of the leaflet which pivot enlargements extend beyond the lateral sides of the leaflet.

DETAILED DESCRIPTION OF THE PREFERRED EMBODIMENT

FIGS. 1-11 show preferred embodiments of a heart valve prosthesis constructed in accordance with principles of the present invention. The heart valve, generally designated 10, is of a bi-leaflet construction, but it will be readily apparent to one ordinarily skilled in the art that the principles of the present invention can be applied to a prosthetic heart valve having single occluder or single leaflet construction. Both embodiments attain improved washing characteristics in the region of the pivot support arrangements, thus preventing stagnation which might eventually lead to clotting.

Referring initially to FIGS. 1-8, heart valve 10 includes a generally annular Valve body 12 and carries a pair of pivoting valve leaflets or occluders 14, which open and close to control the normal flow of blood in the downstream direction of arrows 16 (see FIG. 3). Blood flows through passageway 18 which is defined by a generally cylindrical interior surface or sidewall 20 of valve body 12. Sidewall 20 is interrupted by a pair of diametrically opposed flat wall sections 22. A metal reinforcing ring 23 encircles the outer wall of valve body 12, and is embedded part way therein, to provide additional structural support to the valve body 12. It is preferred that the reinforcing ring 23 be manufactured of a cobalt alloy, and the valve body 12 and valve leaflets 14 manufactured of pyrolytic carbon. The width of the reinforcing ring 23 extends over roughly the center one half of the width of the valve body, with one eighth of the width of the valve body, at opposing ends thereof, not covered by the reinforcing ring. This space at the opposing ends of the valve body accommodates suitable retaining rings (not shown) or the like which retain the cloth of the sewing cuff (also not shown).

As best seen in FIGS. 3 and 6, projections 24 integral with sidewall 20 extend inwardly therefrom. At least a portion of each of these projections 24 is integral with the flat wall section 22, and extends generally perpendicularly therefrom. With particular reference to FIG. 6, the projections 24 each have an arcuate surface 26 and are positioned with respect to one another such that these arcuate surfaces define a recess or socket 28 of circular cross section therebetween. This socket 28 defines the region in which the leaflets 14 are pivotally mounted within the valve body 12 so as to pivot about pivot axis 29, as described further, below.

Referring to FIGS. 3 and 7, the illustrated leaflets 14 are of generally uniform thickness, but it is readily apparent that leaflets having varying thickness could be employed as well. The leaflets 14 have an upstream surface 30 and an opposed, downstream surface 32, with respect to the direction of blood flow. With particular reference to FIG. 3, the leaflets 14 have an arcuate major edge 34 which is located at the downstream end of a fully opened leaflet. A shorter minor masking edge 36 is located at the opposite, upstream end of the leaflets (again, with reference to leaflets in their open position). The curvature of the arcuate major edges 34 corresponds with the curvature of the interior sidewall 20, such that no blood flows between the major arcuate edges and the interior sidewall when the valve is in its closed position. The minor edge 36 of each leaflet is preferably of a straight-line or rectilinear configuration so as to present a relatively flat mating surface to the opposing leaflet upon closing. Furthermore, minor mating edges 36 are truncated such that they are at an angle of about 45° to 60°, and preferably at about 55° with respect to upstream surfaces 30.

With particular reference to FIG. 7, leaflet 14 includes a pair of opposed, lateral edge surfaces 38 which are interposed between the major arcuate edge 34 and the minor mating edge 36. The lateral edge surfaces 38 are preferably flat surfaces and provide minimal clearances with the respective flat wall sections 22 of the valve body interior sidewall.

As best seen in FIGS. 7-11, leaflets 14 also have pivot enlargements or bosses 40 formed therein at the opposing lateral edge surfaces 38. These pivot enlargements are preferably of circular cross section, and a variety of shapes having this characteristic are suitable for use in accordance with the present invention. Examples of pivot enlargement shapes having circular cross section which are suitable for use in the present invention are illustrated in FIGS. 7, 9, 10 and 11 which depict cylindrical, spherical, frustoconical, and protruding frustoconical pivot enlargements, 40a, 40b, 40c, and 40d, respectively The preferred embodiment is depicted in FIG. 7 in which the outer ends of the cylindrical pivot enlargements 40 are flush with the flat lateral edge surfaces 38 of the leaflet and the inner ends of the pivot enlargements taper off smoothly into the leaflet body 14. Tapering of the inner ends of the pivot enlargements minimizes the cross-sectional area of the pivot enlargements exposed to blood flow, thus minimizing drag upon blood flowing through the heart valve 10. The cylindrical enlargements 40 are positioned with their central axes along a common line and generally perpendicular to the lateral edge surfaces 38 of the leaflets 14. FIG. 7A is a cross-sectional view of pivot enlargement 40 showing the tapering of the pivot enlargement into the leaflet body. FIG. 7B shows a cross section of a second, alternative embodiment wherein the outer ends of the pivot enlargement 40' are relieved or chamfered slightly, e.g. at an angle of about 2° to about 5°, in the region along the lateral edge surfaces 38 of the leaflet. The chamfers thus provide two surfaces that are inclined to the flat lateral edge surfaces 38, extending immediately from respective edges thereof on each side of the leaflet and intersecting the cylindrical surfaces sections of the enlargements 40' at oblique angles, as illustrated in FIG. 7B. As a result of these reliefs in the pivot enlargements 40' along the leaflet lateral edge surfaces 38, the flat lateral edge surfaces are of constant width so that the barrier past which blood must flow in the closed condition is uniform across the pivot region and equal to the thickness of the leaflet. As best seen in FIG. 7C, the chamfering of the enlargements 40' removes slices from the radially outer ends of the enlargements, leaving the inclined surfaces that permit blood access (in the totally closed position) along the length of each constant thickness, flat, lateral edge surface of the leaflet. Thus, there will be more uniform blood flow between each leaflet lateral edge surface 38 and the adjacent flat wall section 22 in the region of the pivot, resulting in more effective washing of the leaflet lateral sides and flat wall section in this region.

A third embodiment of the pivotal enlargement is depicted in FIG. 9 which shows a leaflet 14 having spherical pivot enlargements 40b. As seen in the drawing, the spherical pivot enlargements 40b are truncated and positioned at the lateral sides 38 so that the truncated sides of the spheres and the lateral sides of the leaflets form continuous, smooth surfaces. A valve body formed with integral protrusions having complementary surfaces is used with such enlargements.

A fourth alternative embodiment of the pivotal enlargement is depicted in FIG. 10 which shows a leaflet 14 having frustoconical pivot enlargements 40c. The frustoconical pivot enlargements 40c are positioned with their central axes generally along a common line and generally perpendicular to the lateral sides 38 of the leaflets 14. The truncated vertex of each frustoconical pivot enlargement 40c is positioned at the lateral side edge 38 of the leaflet 14 and the truncated surface is relieved at about a 2° angle so the end surfaces of the frusta slope away from the lateral side edge of the leaflet as in the FIG. 7B embodiment. The bases of the frustoconical enlargements, opposite the truncated vertices, are tapered smoothly into the leaflet body.

Still a fifth alternative embodiment is depicted in FIG. 11 which shows a leaflet 14 having frustoconical pivot enlargements 40d which are similar to frustoconical pivot enlargements 40c except in that the truncated apexes extend beyond the leaflet lateral edge surfaces 38 a very slight distance. This embodiment provides a slight additional amount of washing in the regions between the leaflet lateral edge surfaces 38 and the flat wall sections 22 of the valve body.

The pivot enlargements 40 preferably extend in from the leaflet lateral edge surfaces 38 only a short distance; the distance preferably does not exceed the height of projection 24 measured from the flat wall section of the sidewall 22. This is to minimize the area exposed to the blood stream, thus minimizing drag upon blood flowing through the heart valve 10 to preserve good blood flow characteristics.

As best seen in FIG. 3, in the preferred embodiment the portion of each leaflet lying upstream of the pivot enlargements is flat, while the portion lying downstream of the pivot enlargements is curved. The downstream portions of the leaflets are curved such that the upstream surfaces 30 of the leaflets have a concave region 42 of two-dimensional curvature, thus resembling a curved sheet. The opposing downstream surfaces 32 of the leaflets are, accordingly, convex and these regions 44 may have a curvature resembling a paraboloid, an ellipsoid or some other smoothly curved shape. As used herein, a two-dimensional curved surface is one which comprises a plurality of straight lines which define a curved surface, each of which lines is parallel to a straight line axis. Thus, planes including the axis will cut the two-dimensional surface along straight lines, and planes perpendicular to the axis will cut the two-dimensional surface along curved lines. In the preferred embodiment the flat, upstream portions of the leaflets and the curved, downstream portions of the leaflets (with reference to the leaflets in their open position are blended so as to be continuously smooth, without interruptions or discontinuities.

Referring now to FIG. 6, the preferred embodiment of the projections 24 extending inward from the interior sidewall 20 will now be discussed. These projections 24 serve to support the leaflets 14; to define the extent of opening of the leaflets, thus fixing one end of their travel; and to define channels therebetween to provide washing of the pivot enlargements 40 upon pivoting of the leaflets 14.

FIG. 6 shows the interior sidewall 20 of the valve body interrupted by one of the two diametrically opposed flat wall sections 22 of the interior sidewall 20. Eight projections 24 extend inward from the interior sidewall in the region of each of the two flat wall sections 22.

The arcuate sides 26 of each of these projections is integral with, and extends perpendicularly from, the flat wall section 22. The interior end surfaces 46 of the projections 24, which oppose the sidewall, each preferably lie in a common plane which is parallel to the plane defined by the flat wall section 22 of the interior sidewall 20. The remaining sides 48 of each projection 24, which extend between the interior sidewall 20 and interior end surfaces 46, are all preferably perpendicular to the flat wall section 22 of the interior sidewall 20.

Four projections, 24a through 24d, are arranged on one side of the flat wall section such that the arcuate surfaces thereof define a socket 28 for receiving leaflet pivot enlargements 40. The other four of the eight projections are similarly arranged on the other side of the flat wall section 22 and mirror the first four projections. Thus, the flat wall sections 22 of the interior sidewall 20 have two sets of four projections each, wherein each set defines a socket 28 for receiving a leaflet pivot enlargement 40.

As shown in FIGS. 3 and 6, the region between the two sets of projections comprises a central channel 50. The regions between adjacent projections 24 define channels 52 through which blood flows to minimize stagnation in the region of projections 24. These channels 52 are referenced in accordance with the projections which define them; thus, the channel between projections 24a and 24b is referenced as channel 52ab. Therefore, with reference to FIGS. 3 and 6, the four projections on the left side of flat wall section 22 define channels 52ab, 52bc, 52cd and 52da; and the four projections on the right side of the flat wall section 22 similarly define channels 52ab, 52bc, 52cd and 52da.

Referring briefly to FIG. 3, channels 52ab and 52cd are oriented at an angle of between approximately 135° and 165° with respect to the direction of downstream blood flow (indicated by arrows 16). Additionally, channels 52ab and 52cd are generally axially aligned with one another. This same orientation of the channels is present with respect to channels 52ab and 52cd on the right side of the flat wall section.

Referring again to FIG. 6, projections 24a and 24b extend integrally outward from both the curved section of interior sidewall 20 and the flat wall section 22; whereas, projections 24c and 24d are independent of the curved portions of the interior sidewall and are only integral with the flat wall section 22. The upstream sides of projections 24a are flush with the upstream end 54 of the valve body 12.

In order to minimize drag upon blood flowing through the heart valve, the downstream surfaces 51 of projections 24b and 24c are tapered. As seen in FIG. 6, the downstream surfaces 51 of projections 24c taper down toward the interior sidewall 20 such that they taper off completely at the downstream end 56 of the valve body 12. Furthermore, as seen in FIGS. 3 and 6, the downstream sides of projections 24c are also tapered such that central channel 50 widens at the downstream end 56 of the valve body 12. Additionally, the downstream surfaces 51 of projections 24b taper toward the central channel 50, at an angle of between approximately 35° and 75° with respect to the direction of downstream blood flow indicated by arrows 16, over that portion which is integral with the flat wall section 22.

With reference to FIGS. 1, 2, 3, 6 and 8, the operation of the heart valve 10 will now be described. As discussed previously, the pivot enlargements 40 are inserted into the sockets 28 defined by the arcuate portions 26 of the projections 24 such that the leaflets 14 can pivot freely about pivot axis 29. The valve body can be squeezed in a direction perpendicular to the pivot axes to cause it to be distended sufficiently to facilitate such insertion; thereafter, the metal stabilizing ring or reinforcing ring 23 is installed. The leaflets are dimensioned so that there is a loose-fit tolerance between the lateral sides 38 and the flat wall sections 22 of interior sidewall 20. Thus, the leaflet lateral sides 38 pivot adjacent the flat wall sections 22, with a slight recess between the leaflet lateral edge surfaces 38 and the flat wall section 22 (see FIGS. 4 and 5). This recess between the leaflet lateral edge surfaces 38 and the flat wall section 22 allows for the passage of blood therebetween throughout the operation of the valve, thus providing washing of the leaflet lateral edge surfaces 38 and flat wall section 22.

The leaflets 14 are mounted in the valve body 12 by applying forces at diametrically opposed ends of the valve body, indicated by axis 3—3 of FIG. 1, toward the center of the valve body. This results in a reduced diameter along axis 3—3 with a corresponding increase in diameter between diametrically opposed flat wall sections 22. This increase in distance between opposing flat wall sections 22 is sufficient to allow the leaflets 14 to be inserted therebetween. The leaflets are positioned in the valve body 12 such that the pivot enlargements 40 on opposing sides of the leaflets are inside the sockets 28 on opposing sides of the valve body. Then the force on the valve body is removed causing the opposing flat wall sections 22 to return to their original distance with respect to one another, thereby securing the pivot enlargements 40 within the sockets 28. Subsequently, the metal reinforcing ring 23 is installed upon the exterior of the valve body 12, preferably by shrink-fitting, to provide additional structural support and stabilize the right circular cylindrical configuration of the valve body 12.

Assuming an initial, fully closed position, such as that illustrated in FIGS. 1, 3, and 8, when the cardiac cycle reverses, blood flows through the valve body 12 in the downstream direction of arrows 16. Due to the eccentric location of the pivot enlargements 40, a relatively large moment arm is developed between the pivot axis 29 and the center of the arcuate, major mating edge 34. The leaflets 14 then begin to swing in the direction of valve opening, with their minor mating edges 36 being spread apart, and the major arcuate edges 34 being advanced toward one another. The angular orientation of minor mating edges 36 with respect to the upstream surfaces 30 of the leaflets may provide some additional opening force due to blood impacting on minor mating edges 36.

Referring now to FIGS. 2 and 3, the opening movement of the leaflets is stopped when the upstream surfaces 30 thereof contact the seating sides 58 of projections 24a which sides face central channel 50 and the downstream surfaces 32. The seating sides 58 are preferably oriented in a direction parallel to the direction of blood flow indicated by arrows 16 so as to orient the upstream portions of the fully open leaflets in a direction which presents minimal cross-section to the blood flow. This fully open position is shown in FIG. 2 and illustrated in phantom in FIG. 3. The initial pivoting of the leaflets toward their fully open position is relatively rapid, with the rate of pivoting decreasing as the leaflets move further toward their fully open position with less leaflet cross-sectional area exposed to the flow of blood.

Upon reversal of the cardiac cycle, blood flows through the valve body in the upstream direction generally opposite that of arrows 16 of FIGS. 3 and 6. Referring initially to FIG. 3, the upstream force of backflow of blood against the convex surface regions 44 of the leaflet downstream surfaces 32 initiates pivoting of the leaflets in a closing direction. As the leaflet downstream surfaces 32 become positioned more transverse to the backflow of blood, the rate of closing increases until the leaflets come to rest in a fully closed position. The fully closed position of the valve 10 is defined by abutment of major arcuate edges 34 of the leaflets 14 with interior sidewall 20 of valve body 12 which may or may not have a seating region formed therein. The valve body 12 and leaflets 14 are preferably proportioned so that, in addition to abutment of the major arcuate edge and interior sidewall, the minor mating edges 36 of opposing leaflets abut one another when the valve is in its fully closed position. Therefore the flow of blood is blocked between abutting minor mating edges 36 of opposing leaflets as well as between abutting major arcuate edges 34 and the interior sidewall 20 of the valve body, thereby essentially blocking all backflow of blood through the valve except in the regions between the leaflet lateral sides 38 and flat wall sections 22, and the channels 52.

Referring now to FIG. 8, there is a tolerance between the pivot enlargements 40 and sockets 28 such that the pivot enlargements are displaced slightly within the sockets upon reversals of blood flow. Thus, when blood flows in the upstream direction (opposite that of arrows 16) causing the valve to close, the pivot enlargements shift to the upstream side of the socket as shown in FIG. 8. In the fully closed position, depending upon the leaflet configuration and tolerances, the pivot enlargements 40 may abut the surfaces of projections 24a and 24d and not contact projections 24b and 24c.

Whereas prior art arrangements for supporting the leaflets and valve body employed projections which more completely surrounded the pivot enlargements, the support arrangement of the present invention includes channels 52 between a plurality of adjacent projections 24 which provide improved washing characteristics in the region of the support arrangement.

The flow of blood through the channels 52 will be described with reference to the leaflet and projections on the left side of the valve as shown in FIG. 3; however it is readily apparent that blood flow through the channels on the right side of the valve is the same as that through the left side.

Assume an initially open valve, as indicated in phantom in FIG. 3, with blood flowing therethrough in the downstream direction as indicated by arrows 16. The downstream force of the blood upon the leaflets 14 shifts the pivot enlargements 40 of the leaflets downstream within the sockets 28 into contact with projections 24b and 24c, and away from contact with projections 24a and 24d. Some of the blood flowing downstream flows through the recess between pivot enlargement 40 and projection 24d and then into channel 52cd.

Upon reversal of the direction of blood flow through the valve to the upstream direction, the leaflet pivot enlargements 40 are initially displaced slightly upstream within the socket 28 such that the pivot enlargements 40 abut projections 24a and 24d and no longer abut projections 24b and 24c. Simultaneously, the leaflets begin to pivot toward their closed position. Some blood may initially flow into the recess between pivot enlargement 40 and projection 24b and then into channel 52ab.

Upon further blood flow in the upstream direction, the leaflets 14 pivot to their fully closed positions, wherein blood flow in the upstream direction is essentially blocked. (See FIG. 3) In this position, a pressure gradient between the downstream end 56 and the upstream end 54 of the valve body is developed. This pressure gradient results in blood being forced from channel 52bc, into the recess between leaflet pivot enlargement 40 and projection 24b into channel 52ab. Blood is also forced from channel 52cd, into the recess between pivot enlargement 40 and projection 24d into channel 52da.

The greatest washing will occur at the moment the leaflets reach their fully closed position. At this moment the dynamic force of the flowing blood is at its greatest. This inertia from the flowing blood, combined with the pressure differential between the upstream end 54 and downstream end 56 of the valve, results in some blood spurting through the channels 52, even though the upstream flow of blood is substantially blocked.

Prior art arrangements for supporting the leaflets and valve body did not include channels 52ab nor 52cd; thus blood was essentially required to pass from channel 52bc completely through to channel 52da to provide washing in the region between the pivot enlargements 40 and projections 24. The addition of channels 52ab and 52cd results in greater washing of the leaflet support arrangement because a lesser pressure gradient is required to force blood from one channel to an immediately adjacent channel, say between channels 52bc and 52ab, than is required to force blood from one channel to a second channel at the opposing end of the pivot enlargement, say channel 52bc to channel 52da. Thus, the heart valve of the present invention provides effective washing in the region of the support arrangement even with low blood pressures.

Upon the next reversal of the direction of blood flow, back toward the downstream direction of arrows 16, the leaflets are displaced slightly downstream with their pivot enlargements 40 abutting projections 24b and 24c and recessed from projections 24a and 24d. The leaflets simultaneously begin to pivot toward their open position.

Upon further blood flow in the downstream direction, the leaflets pivot to their fully open position, shown in phantom in FIG. 3, whereupon the cycle discussed above repeats itself. Thus, all surfaces inside the valve body 12, including pivot enlargements 24 and projections 40, are washed by blood during each cycle of operation of the heart valve. This washing minimizes the possibility of stagnation within the valve, which could otherwise lead to eventual clotting.

It can be seen from the above that the embodiments of a heart valve 10 constructed according to principles of the present invention obtain substantial advantages, including a heretofore unattainable washing in the region of the support arrangement connecting pivoting leaflets to the valve body.

A description of the present forms of the invention having been described by way of example, it is anticipated that variations of the described forms of the apparatus may be made without departing from the invention and the scope of the appended claims. For example, the downstream surfaces 51 of projections 24c are shown tapered into the interior sidewall 20, and in order to allow for smoother blood flow through the valve 10 other surfaces of the projections which extend into the interior of the valve can also be tapered toward the interior sidewall 20 as well, without departing from the inventive concept of the support arrangement.

Particular features of the invention are emphasized in the claims which follow.

What is claimed is:

1. A prosthetic heart valve, comprising:
   a generally annular valve body having an interior sidewall which defines a central passageway therethrough for the passage of blood in a downstream direction,
   a pair of leaflets each having an upstream surface and a downstream surface, which leaflets are mounted in said valve body so as to alternately permit the flow of blood therethrough in a downstream direction and block the reverse flow of blood in an upstream direction, said leaflets each having a pair of opposite lateral edge surfaces each respectively extending between a minor mating edge and a major arcuate edge;
   said valve body and leaflets having a support arrangement with said leaflets having enlargements of circular cross-section adjacent each lateral edge surface, and said valve body having a plurality of projections extending generally radially inward from said sidewall defining sockets into which said enlargements are received such that said leaflets substantially pivot about eccentric axes between an open position and a closed position where reverse blood flow is blocked;
   adjacent ones of said projections having spaces surfaces defining channels for the passes of blood to provide washing in the region of said support arrangement.

2. A prosthetic heart valve in accordance with claim 1 wherein said sidewall includes diametrically opposed flat sections with at least a portion of each of said projections integral with, and extending generally perpendicular from, the flat sidewall section.

3. A prosthetic heart valve in accordance with claim 2 wherein said valve body includes four of said projections extending inward from each of said diametrically opposed flat sidewall sections which projections said sockets that receive said enlargements.

4. A prosthetic heart valve in accordance with claim 3 wherein a central channel is defined between said four projections which partially define said sockets at each flat sidewall section.

5. A prosthetic heart valve in accordance with claim 2 wherein said lateral edge surfaces of the leaflets are flat and pivot adjacent said flat sidewall sections.

6. A prosthetic heart valve in accordance with claim 1 wherein each of said projections has one side which is arcuate in configuration.

7. A prosthetic heart valve in accordance with claim 1 wherein said projections have sides which are locates so as to abut said upstream and said downstream surfaces of said leaflets and define the extent of opening and closing movement of said leaflets.

8. A prosthetic heart valve in accordance with claim 1 wherein said enlargements in the leaflets terminate at the leaflet lateral edge surfaces.

9. A prosthetic heart valve in accordance with claim 8 wherein said enlargements each have substantially cylindrical surface sections.

10. A prosthetic heart valve in accordance with claim 8 wherein said enlargements in said leaflets have substantially spherical surface sections.

11. A prosthetic heart valve in accordance with claim 8 wherein said enlargements in said leaflets have substantially conical surface sections.

12. A prosthetic heart valve in accordance with claim 1 wherein said valve body interior sidewall had a pair of diametrically opposed flat sidewall sections from which said projections extend generally radially inward, wherein said leaflet lateral edge surfaces are flat, of substantially constant width, and face said flat sidewall sections, and wherein said enlargements are relieved in the regions radially inward of the leaflet lateral edge surfaces so as to provide blood access adjacent said flat edge surfaces.

13. A prosthetic heart valve, comprising:
a generally annular valve body having an interior sidewall which defines a central passageway therethrough for the passage of blood in a downstream direction,
occluder means mounted in said valve body so as to alternately permit the flow of blood therethrough in a downstream direction and block the reverse flow of blood in an upstream direction, said occluder means having a pair of opposite straight lateral edge surfaces respectively extending between a minor edge and a major arcuate edge;
said valve body and occluder means having a support arrangement with said occluder means having enlargements of circular cross-section adjacent each lateral edge surface, and said valve body having a plurality of projections extending generally radially inward from said sidewall at generally diametrically opposed locations defining sockets into which said enlargements are received such that said occluder means substantially pivots about an eccentric axis between an open position and a closed position where blood flow is blocked;
adjacent ones of said projections having surfaces defining channels for the passage of blood to provide washing in the regions of said support arrangement and past said lateral edge surfaces within said sockets.

14. A prosthetic heart valve, comprising
a generally annular valve body having an interior sidewall which defines a central passageway therethrough for the passage of blood in a downstream direction, said valve body sidewall having a pair of diametrically opposed flat sidewall sections,
a pair of leaflets each having an upstream surface and a downstream surface, which leaflets are mounted in said valve body so as to alternately permit the flow of blood therethrough in a downstream direction and block the reverse flow of blood in an upstream direction, said leaflets each having a minor mating edge surface, a major arcuate edge surface, a pair of opposite lateral edge surfaces respectively extending therebetween, and
said valve body and leaflets having a support arrangement with said leaflets having enlargements of circular cross-section adjacent each lateral edge surface, and with said valve body having a plurality of projections extending inward from said flat sidewall sections defining sockets into which said enlargements are received such that said leaflets substantially pivot about eccentric axes between an open position and a closed position where blood flow is blocked,
said leaflet flat lateral edge surfaces facing said flat sidewall sections and being parallel thereto, and
said enlargements being relieved in the regions immediately radially inward of said leaflet lateral edge surfaces so that said leaflet edge surfaces are of substantially constant width.

15. A prosthetic heart valve in accordance with claim 14 wherein said enlargements each have substantially cylindrical surface sections.

16. A prosthetic heart valve in accordance with claim 15 wherein said reliefs are provided by chamfers in the form of a pair of surfaces which extend from respective edges of each said leaflet lateral edge surface and intersect said cylindrical surfaces at an oblique angle.

17. A prosthetic heart valve in accordance with claim 14 wherein each of said projections has one side which is arcuate in configuration and forms a bearing surface for said socket.

18. A prosthetic heart valve in accordance with claim 17 wherein said projections each have other sides which are located so as to abut said upstream and said downstream surfaces of said leaflets and define the extent of opening and closing movement of said leaflets.

19. A prosthetic heart valve in accordance with claim 14 wherein each of said sockets is formed from four separate projections which are spaced apart from one another so as to define open regions therebetween.

* * * * *

UNITED STATES PATENT AND TRADEMARK OFFICE
CERTIFICATE OF CORRECTION

PATENT NO. : 5,080,669

DATED : 01/14/92

INVENTOR(S) : TASCON, et al.

It is certified that error appears in the above-identified patent and that said Letters Patent is hereby corrected as shown below:

Page 1, under References Cited, under "Bokros", third instance, change "4,880,010" to --4,888,010--.

IN THE SPECIFICATION: Column 2, line 26, after "elements" insert --are--; line 58, "relayed" should be--relieved--.

IN THE CLAIMS: Column 10, line 51, in Claim 1, "passes" should be --passage--; line 63, after "projections", in Claim 3, insert --partially form--. Column 11, line 8, in Claim 7, "locates" should be --located--; line 26, in Claim 12, "had" should be --has--.

Signed and Sealed this

Twenty-seventh Day of April, 1993

*Attest:*

MICHAEL K. KIRK

*Attesting Officer*     *Acting Commissioner of Patents and Trademarks*